United States Patent [19]

Grossman

[11] 4,408,615
[45] Oct. 11, 1983

[54] INTERFERENCE FILTER

[75] Inventor: Hyman Grossman, Buchanan, N.Y.

[73] Assignee: Cambridge Instruments, Inc., Ossining, N.Y.

[21] Appl. No.: 239,469

[22] Filed: Mar. 2, 1981

[51] Int. Cl.³ .............................................. A61B 5/04
[52] U.S. Cl. .................................... 128/696; 128/901
[58] Field of Search ....................... 128/696, 702–710, 128/901, 902

[56] References Cited

U.S. PATENT DOCUMENTS

| | | | |
|---|---|---|---|
| 3,498,288 | 3/1970 | Max et al. | 128/696 |
| 3,902,479 | 9/1975 | Chaumet | 128/703 |
| 4,161,945 | 7/1979 | Grossman | 128/696 |
| 4,243,045 | 1/1981 | Maas | 128/696 |
| 4,331,158 | 5/1982 | Partridge | 128/902 |

Primary Examiner—William E. Kamm
Attorney, Agent, or Firm—Eugene E. Geoffrey, Jr.

[57] ABSTRACT

An interference filter for the removal of power line interference from amplifying systems, such as electrocardiographs, which includes a band-rejection filter tuned to reject the power line frequency interference, a differential amplifier to which the signal being amplified and the output of the notch filter are applied to produce an output consisting of only the interference signal. The interference signal is fed to and stored in a memory which is constantly updated and the output of the memory is then summed with the original signal. Since the phase of the output of the memory is reversed from the interference in the original signal, only the original signal will result. An electronic switch is connected between the output of the differential amplifier and the memory and is operated by a velocity detector connected with the output of the band-rejection filter. If at any time the velocity detector senses a rate of rise of the incoming signal exceeding a selected value, it functions to open the switch for a predetermined period and thereafter closes the switch. This procedure in the case of electrocardiographs, prevents distortion of electrocardiographic signals.

13 Claims, 3 Drawing Figures

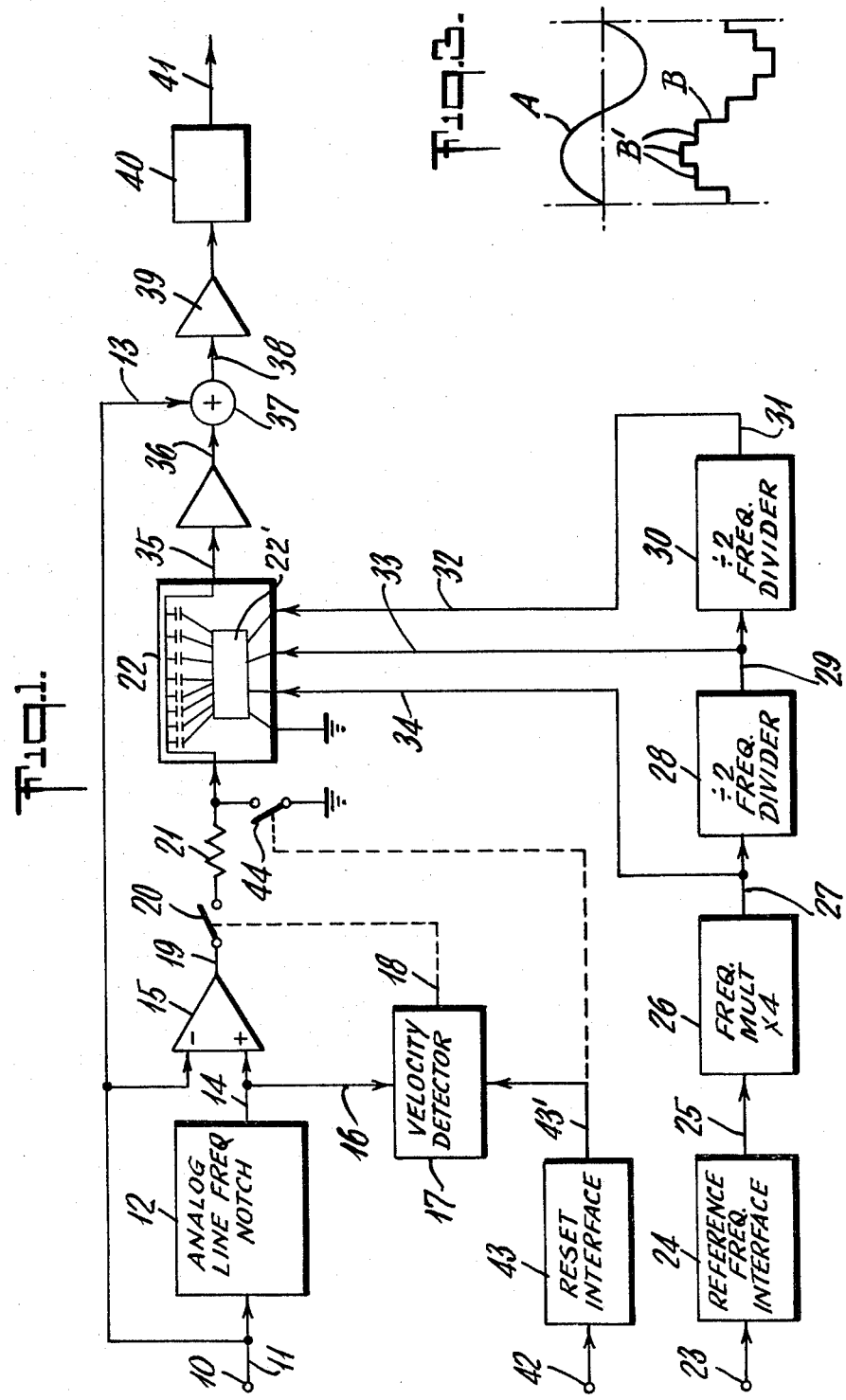

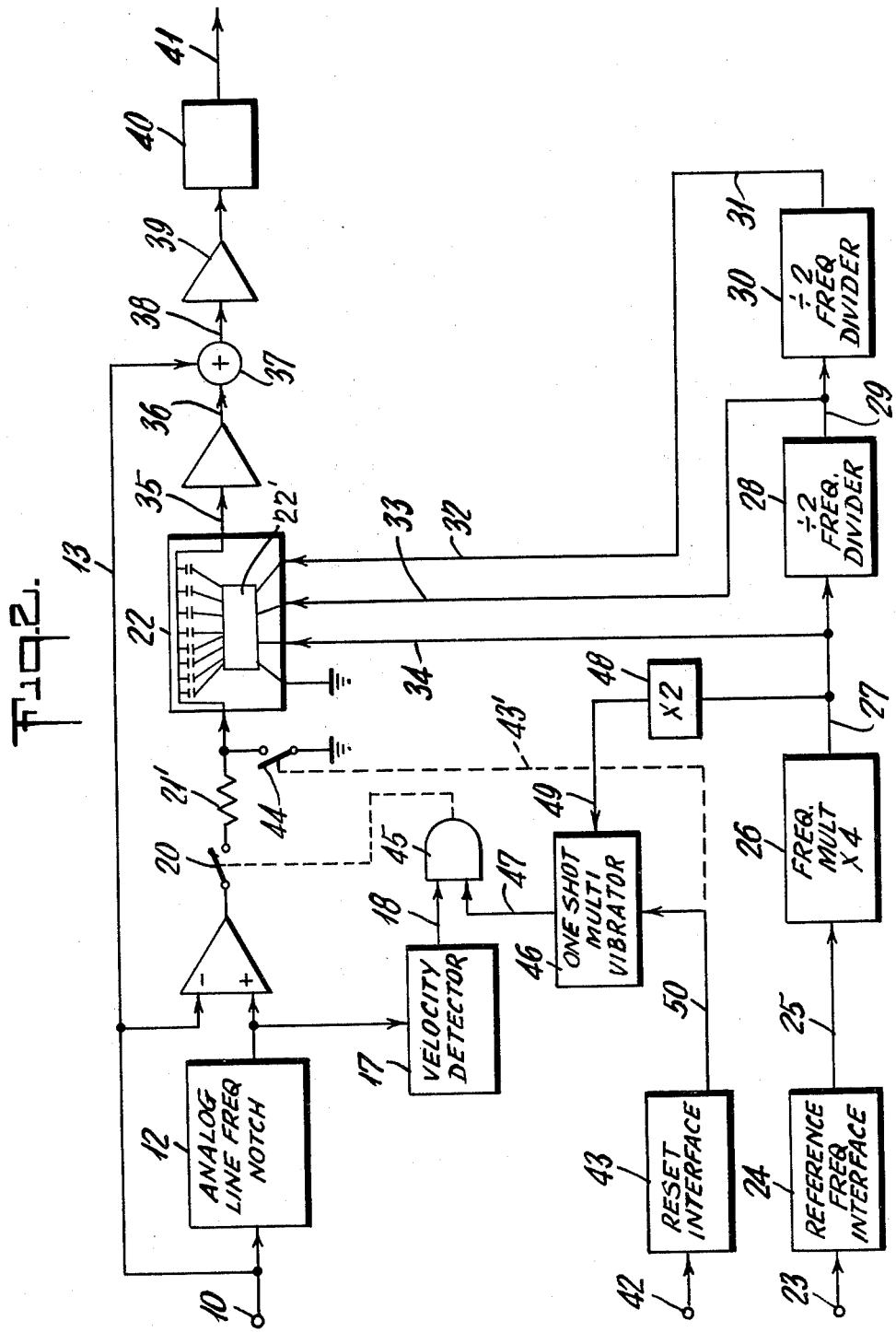

INTERFERENCE FILTER

This invention relates to apparatus for processing electrical signals such as signals produced by electrocardiographs and other similar devices for recording biological and other signals and more specifically to novel and improved circuitry for removal of line frequency interference that functions very rapidly to effect removal of line frequency interference and without distorting the signals being amplified. This is extremely important in electrocardiographs as the heart-wave signals must be reproduced faithfully and should not be affected by power line interference.

In the recording of signals such as electrocardiographic signals, both slowly varying components of small amplitude as well as rapidly varying components of significantly greater amplitude are involved. Power line hum while being of low amplitude with reference to the electrocardiographic signals nevertheless tends to obscure the slowly varying components of the electrocardiographic signal. Moreover, such interference may also modify the characteristics of the electrocardiographic signals with the result that faithful reproduction is not always obtained. In present day electrocardiographs, signals from a plurality of leads connected to a patient are successively recorded and each lead or lead combination may have different interfering signals. Thus when lead combinations are switched periodically, it is essential that the apparatus compensate for changing conditions of the interference.

Interference filters particularly for use in connection with electrocardiographs have been known and one such filter is disclosed is U.S. Pat. No. 4,161,945. The filter of that patent essentially includes a notch filter together with a velocity detector, the latter detecting the presence and absence of a rapid rate of change of the electrocardiographic signal. The control signals function to actuate switch means to selectively feed the electrocardiographic signals through the notch filter under certain conditions and to bypass the notch filter under other conditions. While this device has been found effective, it does not remove interference during the actual presence of electrocardiographic signals having a relatively rapid rate of change. Another prior known device is the digital filter which while capable of removing interference only without introducing attenuation or phase distortion nevertheless requires several seconds before the interference is completely removed from the electrocardiographic signal. Such a filter is therefore unacceptable particularly in instances wherein electrocardiographic leads are switched at intervals of the order of 10 seconds. Under such conditions at least 3 or more seconds of a recording will contain undesirable interference.

This invention overcomes the difficulties with prior known devices and provides novel and improved circuitry which will not only remove line frequency interference but will also function within approximately 100 milliseconds after each lead switching operation to completely remove interference without distorting the electrocardiographic signals.

Another object of the invention resides in the provision of a novel and improved interference filter particularly useful with electrocardiographs which provides highly reliable and stable circuitry and which substantially instantaneously responds to the level of interference on any lead combination to effectively and completely remove such interference without distortion of the desired signals.

Still another object of the invention resides in the provision of a novel and improved interference filter which is characterized by its simplicity and ease with which it may be adapted to meet the requirements of a variety of applications.

The interference filter in accordance with the invention comprises a circuit wherein the interference is removed from the signal and the latter is fed to a velocity detector. The velocity detector normally produces a signal of one magnitude but if the input signal has a component having a rate of change exceeding a preselected rate, the velocity detector will produce a second signal of different magnitude. The interference is filtered from the signal and fed through a switch, controlled by the velocity detector, to a memory which stores the interference and also constantly updates the magnitude thereof. The output of the memory is summed with the original signal containing interference so that the interference signal produced at the output of the memory will cancel the interference contained in the original signal. The velocity detector functions to maintain the switch in a closed position under normal conditions, that is when the signal entering the velocity detector does not contain any components wherein the rate of rise exceeds a predetermined value. However should the rate of rise of the signal fed to the velocity detector exceed the selected rate of rise, the switch will open and prevent the introduction of new information into the memory. A second switch is connected between the input of the memory and ground for clearing the memory in the event a new input having a different magnitude of interference is applied to the input of the interference filter. The invention may further include means for closing the first switch at a rate coordinated with the characteristics of the memory and the interference frequency.

The above and other objects of the invention will become more apparent from the following description and accompanying drawings forming part of this application.

IN THE DRAWINGS

FIG. 1 is a block diagram illustrating one embodiment of the invention;

FIG. 2 is a block diagram illustrating another embodiment of the invention; and

FIG. 3 illustrates the operation of the memory to store information pertaining to the interference.

In as much as the circuits now to be described are principally intended for use with electrocardiographic equipment, they will be described in connection with that application though it will become evident as the description proceeds that it is equally useful with any type of electronic equipment where it is desired to remove power line hum and other similar interference.

Referring now to FIG. 1 showing one embodiment of an interference filter particularly useful in removing interference from an electrocardiograph, the signals from a plurality of electrocardiograph leads are successively applied to the input terminal 10 and then fed through the conductor 11 to a band rejection filter 12 having a −3 db rejection range, when utilizing 60 Hertz power, of 50 to 70 Hertz. The filter output 14 then consists of the electrocardiographic signal less the power line interference and this is fed to the non-inverting input of a unity gain differential amplifier 15. At the same time, the output signal of the filter 12 is fed through the conductor 16 to the input of a velocity detector which is described in detail in U.S. Pat. No. 4,161,945. Briefly, the velocity detector in one form will produce an output signal in the absence of signals having a rate of rise exceeding a preselected value. Upon the occurrence of a signal having a rate of rise exceeding the selected value, the velocity detector will automatically become inactivated. The output of the velocity detector appears on the broken line conductor 18.

The electrocardiographic signal including the interference on the conductor 13 is fed to the inverting input of the amplifier 15 with the result that the electrocardiographic signal will be cancelled leaving only the interference signal on the output conductor 19. Since the electrocardiographic signal together with the interference is fed to the inverting input of amplifier 15, the interference signal appearing on the conductor 19 will be inverted or reversed in phase.

The inverted interference signal on the conductor 19 is fed through a switch 20, illustrated here as a mechanical switch for purposes of simplicity but in actual practice may be a solid state device such as a junction FET. The output of the switch is fed through a resistor 21 to a memory 22.

With the apparatus thus far described and with the output of the velocity detector 18 coupled to the switch 20, the velocity detector will normally maintain the switch 20 in a closed position so that the inverted interference signal will be fed constantly to the memory 22. Upon the presence of a signal in the velocity detector such as the electrocardiographic signal which will have a high rate of change, the velocity detector is inactivated and the switch 20 is opened. This prevents updating of the information in the memory 22 during the time that the velocity detector is inactivated. A time delay network incorporated as part of the velocity detector maintains the detector in an inactivated condition for a period of about 50 milliseconds after the rapidly changing portion of the electrocardiographic wave has passed whereupon it is automatically reactivated to close the switch 20.

The memory 22 is in the form of a digitally controlled, single pole, eight position analog switch including eight capacitors and wherein the wiper is connected to ground. In the instant embodiment of the invention, timing signals for the memory 22 are generated by applying a line frequency reference to the input terminal 23. This signal is fed through a buffer amplifier or interface 24 through the conductor 25 to a frequency multiplier 26. The multiplier 26 multiplies the line frequency by 4 so that in the case of 60 cycles the frequency appearing on the conductor 27 will be 240 cycles. This frequency is then fed to a divider 28 and the output 29 will be at 120 cycles. This output is fed to a second divider 30 and the output 31 of the second divider is 60 cycles. The three frequencies namely 60, 120 and 240 are fed through the conductors 32, 33 and 34 respectively to the memory 22. Since the memory includes eight capacitors, these timing signals will activate the wiper of a digitally controlled, eight position switch forming part of the memory and sequentially record the interference signal in steps as illustrated in FIG. 3. Each capacitor will be sequenced once during each power line and always at the same point in the cycle by the switch. As a result, each capacitor will store the average voltage of the interference signal present during the period when it is being sequenced. In FIG. 3, the curve A represents one cycle of line frequency hum interference and the curve B illustrates the voltage steps B' recorded in the memory corresponding to the sign wave A. The output 35 of the memory is constantly fed through a buffer amplifier and its output signal, on the lead 36, is summed with the signal appearing on the lead 13 at the summing junction 37. Since the signal appearing on the lead 36 representing the interference is inverted with reference to the interference appearing on the conductor 13, the signal appearing on conductor 38 will include only the electrocardiographic signal and all interference will be cancelled. The signal on lead 38 is then processed through the buffer amplifier 39 and through a low pass filter 40 to remove any high frequency interference that may have been produced by the operation of the memory. The output 41 is then fed to conventional electrocardiographic equipment to affect recording of the signal in a suitable manner.

As previously pointed out in the operation of electrocardiographs, means are generally employed for automatic switching of the leads from the patient. That is, different lead combinations are successively recorded in order to obtain complete diagnostic information. Since different combinations of leads are utilized, the interference appearing on each lead will often be of different magnitude. Accordingly, when each successive lead or combinations of leads is applied to the input 10, a reset signal is applied to the terminal 42. This signal is fed through an interface or buffer amplifier 43 and lead 43' and functions during the interchange period to close a switch 44. While the switch 44 is shown as a mechanical switch, it would normally be an electronically operated switch such as a junction FET or the like. In so doing, closure of the switch during the operation of the memory will automatically clear all information from the memory. At the same time, the reset signal is also applied to the velocity detector to retain the switch 20 in the open position. This operation takes approximately 20 milliseconds whereupon the switch 44 is opened and the velocity detector activated to permit new interference information to be fed to the memory 22. The resistor 21 functions as a averaging element in that it controls the charging rate of each of the capacitors in the memory to maintain minimum phase shift between the stored signals and the interference on conductor 13.

With the circuit as described above, power line interference is effectively eliminated from the electrocardiographic signal. Moreover, during the actual presence of a high velocity portion of the electrocardiographic signal, updating the memory is interrupted to avoid the possibility of distortion of the electrocardiographic signal. However, the information retained in the memory will continue to be fed from the output of the memory 22 and cancel the interference appearing with the electrocardiographic signal based on information recorded in the memory just prior to the arrival of the high velocity portion of the electrocardiographic signal. Thus, effective cancellation of interference is effected without the distortion of the electrocardiographic signal and at the same time the electrocardiographic signal is not distorted in any manner. In addition, the sensitivity of the velocity detector can be adjusted to become inactivated with any given rate of rise appearing on the input signal. In the case of electrocardiographs, excellent results have been achieved if the velocity detector is inactivated upon the presence of a signal wherein the rate of change exceeds 2½ to 3 millivolts per second.

As discussed in connection with the embodiment of the invention illustrated in FIG. 1, an averaging resistor 21 is connected between the output of the differential amplifier 15 and the input of the memory 22. The resistor 21 has a fairly large value of the order of ten's of thousands of ohms so that each of the capacitors in the memory charged through the resistor 21, will receive a charge averaged over several charging periods and thus prevent any material phase shift from occurring in the memory. It is important that the phase shift be maintained at a negligible value in order to provide effective elimination of the interference from the signal at the summing junction 37. A alternate means for the achievement of this end is illustrated in FIG. 2 wherein like numerals have been used to denote corresponding components in the two figures.

In FIG. 2, the output of the velocity detector 17 is fed to one input terminal of an AND gate 45 and the output of the AND gate functions to operate the switch 20 which as previously mentioned may be in the form of a junction FET. A one-shot multivibrator 46 has its output 47 connected to the second input of the AND gate 45 and a pulse train is applied to the one-shot multivibrator from the output 27 of the frequency multiplier 26 through a multiplier 48 which multiplies the signal by 2 thus providing 480 cycles on the conductor 49 for application to the one-shot multivibrator. The frequency of 480 cycles is based on 60 cycle line frequency and therefore with other line frequencies, assuming the memory 22 has eight steps, the pulse rate on the conductor 49 would be eight times the line frequency. In the event the memory 22 includes a different number of capacitors, the multiplying factor for the line frequency would be modified in accordance with the number of such capacitors. In addition to the application of pulses to the multivibrator, a reset pulse is applied from the reset interface 43 through conductor 50 to the one-shot multivibrator and the operation of this circuitry is as follows.

In the case of the first embodiment of the invention, the switch 20 is normally closed and is opened upon the presence of signals in the velocity detector 17 wherein the rate of rise exceeds a predetermined value such as the presence of a heart wave in connection with electrocardiographs. In this embodiment of the invention, the one-shot multivibrator is pulsed 480 times per second, based on 60 cycle line frequency, and thus produces 480, 50 microsecond, pulses per second on the output 47 which is fed to the AND gate 45. Since the velocity detector 17 develops an output signal on the conductor 18 in the absence of an input signal having a rate of rise exceeding a predetermined value, the switch 20 will be closed for a duration of 50 microseconds 480 times per second. Since these pulses are precisely coordinated and timed with the line or reference frequency, they will also be coordinated with the operation of the memory. More specifically, the pulses from the one-shot multivibrator 46 will be centered with respect to each of the plateaus or steps denoted by B' as shown in FIG. 3 and the center of each plateau corresponds precisely to the magnitude of the interference at that particular point in time. Since the charging of each capacitor must occur within a relatively short time duration, the resistor denoted in FIG. 2 by the numeral 21' is of a relatively low value and in actual practice can be of the order of 1,000 to 2,000 ohms. Since the charging duration for each capacitor is materially reduced and since the one-shot multivibrator pulses are precisely centered with reference to each plateau, the interference information stored in the memory will be precisely 180° out of phase with the interference appearing on the conductor 13. This produces precise cancellation of the interference at the summing junction 37.

Upon the switching of lead signals at the input terminal 10, the reset signal applied to the input terminal 42 is fed by way of lead 50 to the one-shot multivibrator. During the presence of a signal on the lead 50, operation of the multivibrator will be inactivated with the result that the switch 20 will remain open. At the same time, as discussed in connection with FIG. 1, switch 44 will be closed and thus erase all information stored in the memory. This procedure is desirable to prevent the output of amplifier 15 from being shorted to ground when switch 44 is closed to clear the memory.

While the invention has been described in connection with devices powered by 60 Hertz alternating current, it is evident that the invention is useful on devices powered by alternating current of other frequencies as well as battery operated devices. In the case of battery operated devices, it is merely necessary to provide a frequency reference and coordinate the reference with the interfering frequency and the memory in the same manner that the memory is coordinated with 60 cycle reference utilized in the foregoing embodiments of the invention.

While only certain embodiments of the invention have been illustrated and described, it is apparent that alterations, changes and modifications may be made without departing from the true scope and spirit thereof.

What is claimed is:

1. An interference filter for the removal of AC interference caused by power lines from a signal containing information to be processed comprising means for filtering said interference from said signal and producing a filtered signal free of interference, means for combining the filtered signal with the unfiltered signal to produce an interference signal, means for reversing the phase of the interference signal relative to the interference in the first said signal and means for combining the last said interference signal with the first said signal to produce a resultant signal wherein the interference is cancelled.

2. An interference filter according to claim 1 including a memory having an input and output and means for feeding said interference signal of reversed phase to the input of said memory, and means for combining the first said signal with the signal produced at the output of said memory to effect cancellation of the interference signal from the first said signal.

3. An interference filter according to claim 2 wherein the first said signal comprises a series of recurrent wave forms, means for amplifying the first said signal and said memory further includes switch means connected in series with the input thereof, a velocity detector having an input and output, means feeding said signal containing information to be processed to the input of said detector, said detector producing an output signal for a predetermined time duration upon the presence of a rate of rise in the first said signal exceeding a predetermined value, and a connection between the output of the velocity detector and said switch means to open said switch means during the presence of said output signal from said velocity detector and cause the stored information in said memory to be repeatedly fed to said combining means during the time the last said switch means is open.

4. An interference filter according to claim 3 wherein the signal fed to the input of said velocity detector is obtained from the output of said filtering means.

5. An interference filter according to claim 3 wherein said memory stores the magnitude of power line interference at successive points in each cycle, and means for controlling said memory by a frequency reference related to the power line frequency.

6. An interference filter according to claim 5 including gating means in series with the output of said velocity detector, pulse generating means in the form of a one shot multivibrator connected to said gating means, means for feeding a power line reference frequency signal to said multivibrator, said gating means responding to the outputs of said multivibrator and velocity detector to repetitively close said switch means at a rate related to the reference frequency, said pulses each having a duration less than the time interval determined by the time duration of one power line cycle.

7. An interference filter for the removal of power line interference in an electrocardiograph amplifying system comprising a band rejection filter for rejecting a frequency band which includes said interference, said filter having an input and output, a differential amplifier having two inputs and an output, means for feeding a signal including said power line interference to the input of said filter and to one input of said amplifier, means for feeding the output of said filter to the other input of said amplifier, said amplifier cancelling the electrocardiographic signal and producing an output containing only said interference, a memory having an input and output, means for feeding said interference to the input of said memory and constantly updating the memory, a summing junction, and means for feeding the contents of said memory and said signal containing said interference to said summing junction thereby cancelling the interference from said signal without material distortion of said signal.

8. An interference filter according to claim 7 including means for sensing the presence of an electrocardiographic signal and means for interrupting the input to said memory during the presence of said electrocardiographic signal whereby cancellation of the power line interference will be based upon the information stored in said memory immediately prior to the arrival of the electrocardiographic signal.

9. An interference filter according to claim 8 wherein said sensing means comprises a velocity detector having a input and output, switch means in series with the input of said memory, a connection between the output of said band rejection filter and the input of said detector and a connection between the output of said detector and said switch means whereby said switch means is normally closed to constantly update said memory and said detector upon sensing a rate of change of at least a given magnitude produced by the presence of at least portions of the electrocardiographic signal opening said switch to interrupt updating of the memory, and time delay means in said detector for maintaining said switch means in the open position for a selected time duration.

10. An interference filter according to claim 9 including a resistor in series with said switch.

11. An interference filter according to claim 10 including means for controlling said memory to cause it to successively record voltage magnitudes at spaced points in each cycle of the power line interference.

12. An interference filter according to claim 11 including gating means in series with the output of said velocity detector, means for producing a pulse train at a periodicity equal to the periodicity of said points of each power line interference cycle with each pulse having a duration substantially less than the time between pulses, and means for feeding said pulse train to said gating means whereby said switch means will be closed only for the duration of each pulse, said velocity detector interrupting closure of said switch means upon the detection of a signal having a rate of rise exceeding a predetermined value.

13. An interference filter according to claim 11 wherein said electrocardiograph includes means for periodically changing the source of the signals from which power line interference is to be removed and producing a reset signal signifying a change in the electrocardiographic signal source, said filter including a switch connecting the input of said memory to ground, means for feeding said reset signal to the last said switch to clear the memory and means for feeding said reset signal to said velocity detector to maintain the first said switch in an open position while the last said switch is closed.

* * * * *